US010350603B2

(12) United States Patent
Zantl et al.

(10) Patent No.: US 10,350,603 B2
(45) Date of Patent: Jul. 16, 2019

(54) COVER DEVICE FOR SAMPLE CARRIER

(75) Inventors: Roman Zantl, Baldham (DE); Elias Horn, München (DE)

(73) Assignee: IBIDI GMBH, Martinsried (DE)

( * ) Notice: Subject to any disclaimer, the term of this patent is extended or adjusted under 35 U.S.C. 154(b) by 0 days.

(21) Appl. No.: 12/352,084

(22) Filed: Jan. 12, 2009

(65) Prior Publication Data

US 2009/0191621 A1 Jul. 30, 2009

(30) Foreign Application Priority Data

Jan. 17, 2008 (EP) ..................................... 08000869

(51) Int. Cl.

*C12M 1/22* (2006.01)
*C12M 3/00* (2006.01)
*B01L 3/00* (2006.01)

(52) U.S. Cl.

CPC ..... *B01L 3/50853* (2013.01); *B01L 2300/041* (2013.01); *B01L 2300/046* (2013.01); *B01L 2300/0627* (2013.01); *B01L 2300/0877* (2013.01)

(58) Field of Classification Search

CPC .................................................. B01L 3/50853
USPC ......... 435/305.1, 287.1–288.5, 305.2, 305.3, 435/305.4; 264/129; 422/503, 547, 552, 422/502, 553; 73/864.91, 863.23; 156/69
See application file for complete search history.

(56) References Cited

U.S. PATENT DOCUMENTS

| | | | | |
|---|---|---|---|---|
| 3,055,808 | A * | 9/1962 | Henderson | B65D 43/0214 435/305.3 |
| 3,745,091 | A * | 7/1973 | McCormick | B01L 3/5085 156/305 |
| 3,835,834 | A * | 9/1974 | Brown et al. | 600/572 |
| 3,913,562 | A * | 10/1975 | Moore et al. | 435/307.1 |
| 4,444,310 | A | 4/1984 | Odell | |
| 5,721,136 | A | 2/1998 | Finney et al. | |
| 6,037,168 | A * | 3/2000 | Brown | 435/288.3 |
| 6,468,788 | B1 * | 10/2002 | Marotzki | C12M 23/10 435/288.3 |
| 6,500,390 | B1 * | 12/2002 | Boulton | B01J 19/0046 215/247 |
| 6,703,120 | B1 * | 3/2004 | Ko | C09J 183/04 428/351 |

(Continued)

FOREIGN PATENT DOCUMENTS

| | | | |
|---|---|---|---|
| DE | 19852946 | A1 | 5/2000 |
| JP | 2005225526 | * | 8/2005 |
| WO | WO2007014739 | * | 2/2007 |

OTHER PUBLICATIONS

Inaba et al, Derwent English abstrast of JP2005225526, Aug. 25, 2005.*

(Continued)

*Primary Examiner* — Kevin Joyner
*Assistant Examiner* — Holly M Mull
(74) *Attorney, Agent, or Firm* — Moore & Van Allen PLLC; Henry B. Ward, III

(57) ABSTRACT

The present invention relates to a cover device for a sample carrier, comprising a sticky surface area for connection to the sample carrier, wherein the sticky surface area is configured such that the sample carrier is covered in liquid-tight fashion after connection of the cover device to the sample carrier in the sticky surface area.

20 Claims, 5 Drawing Sheets

(56) References Cited

U.S. PATENT DOCUMENTS

| | | | | |
|---|---|---|---|---|
| 2004/0214313 | A1* | 10/2004 | Zhang | C12M 23/10 435/288.4 |
| 2005/0072946 | A1* | 4/2005 | Studer et al. | 251/11 |
| 2005/0164373 | A1* | 7/2005 | Oldham et al. | 435/287.2 |
| 2005/0191582 | A1* | 9/2005 | Bietsch et al. | 430/311 |
| 2006/0121298 | A1* | 6/2006 | Wittke | B01L 3/508 428/480 |
| 2010/0175488 | A1* | 7/2010 | Kahl et al. | 73/864.91 |

OTHER PUBLICATIONS

Minkel, Tree frog inspires new easy-off stickies, Oct. 11 2007, Scientific American, pp. 1-4, accessed electronically Nov. 9, 2017 at https://www.scientificamerican.com/article/tree-frog-inspires-new-easy-off-stickies/.*

* cited by examiner

COVER DEVICE FOR SAMPLE CARRIER

FIELD OF THE INVENTION

The present invention relates to a cover device for a sample carrier and a method for producing a cover device or a sample carrier.

BACKGROUND OF THE INVENTION

Especially in the biological, biochemical or medical field, sample carriers are used for analyzing molecules, e.g. DNA, or cells. The substances to be analyzed are in general placed with a liquid in or on a sample carrier and can then be analyzed for example with the help of microscopic methods (transmitted light microscopy, fluorescence microscopy, confocal microscopy, etc.).

A sample carrier in the form of a flow chamber is for instance known from DE 101 48 210. In a base plate said flow chamber comprises at least one channel which is joined at both sides to a liquid reservoir.

To provide suitable sample chambers or reservoirs, different components are often joined together to obtain the desired sample chamber structures in this way. Different methods are known for joining these different components. A possible method is described in EP 1 579 982 where a plastic body is exposed to vapor containing a swelling medium and is then pressed at room temperature against another plastic body.

In this known method a swelling medium that is suited for the respectively used components must be provided for the subsequent solubilization of the surface of the plastic body. It is therefore the object of the present invention to provide a cover device for a sample carrier that can be easily joined to the sample carrier.

BRIEF SUMMARY OF THE INVENTION

This object is achieved by a a sample carrier system that includes a sample carrier and a cover device. The cover device includes a sticky surface area for connection to a surface of the sample carrier. The sticky surface area is configured such that a covered portion of the sample carrier is covered in liquid-tight fashion by connection of the sticky surface area of the cover device to the surface of the sample carrier. The cover device also includes at least one cover element for covering a surface area of the sample carrier. The at least one cover element is configured such that the surface area of the sample carrier is covered in liquid-tight fashion by connection of the cover device to the sample carrier. The sample carrier includes a sample chamber within the covered portion. At least one of the cover elements is configured for covering a surface area in the interior of the sample chamber.

According to the invention a cover device for a sample carrier is provided, comprising a sticky surface area for connection to the sample carrier, wherein the sticky surface area is configured such that the sample carrier is covered in a liquid-tight manner after connection of the cover device to the sample carrier in the sticky surface area.

Especially on account of the sticky surface area such a cover device offers the advantage that on the one hand it can be connected to the sample carrier at substantially any desired point of time. On the other hand such a cover device can easily be connected to sample carriers consisting of a great variety of different materials.

The sample carrier itself may have very different shapes or geometries. For example it may just be a coverslip or a foil. Alternatively, however, the sample carrier may already exhibit structures for accommodating samples, e.g. a sample chamber or a reservoir.

"Sticky" in this context shall mean that stickiness is observed at room temperature, particularly of 20-25° C., and at 30-40% relative humidity. A sticky state should especially prevail when cover device and sample carrier are joined. After the joining process the cover should also be liquid-tight in the presence of a liquid or a medium or at 100% humidity.

To be more specific, the sticky surface area can be configured such that it is permanently sticky and/or non-curing. This permits repeated joining of the cover device to a sample carrier at least on dry surfaces.

The cover device may comprise a carrier material to which an adhesive layer is applied for forming the sticky surface area.

This allows the structures desired in this manufacturing method for the cover device, particularly of a non-sticky material. The cover device may particularly comprise a blank which includes the carrier material or is made of said material. With this blank the adhesive layer is then applied to predetermined areas.

The adhesive may particularly be a pressure-sensitive adhesive. Such a pressure-sensitive adhesive remains highly viscous and permanently sticky after application to the carrier material. The viscosity may particularly be 50-5000 mPa·s. Such a pressure-sensitive adhesive does not cure. The adhesive may be a two-component adhesive with a base material and a cross-linker. Base material and cross-linker may particularly be mixed in an asymmetric ratio.

The sticky surface area may particularly be structured such that it is perpendicular to the surface. The sticky surface area can thus comprise elevations or can be made irregular or non-planar in another way.

For instance, the adhesive layer can be applied by immersing the surface to be rendered sticky into a, for example, freshly mixed pressure-sensitive adhesive and by subsequently pressing the same against a smooth or structured surface for a predetermined period of time. With a structured (stamp) surface it is thus possible to obtain a structured adhesive layer. When e.g. PDMS Sylgard 184 is used as the pressure-sensitive adhesive in a mixing ratio of 35:1 and structured plastic as the casting surface, microstructures, such as channels, can for instance be formed by this. Such structures may e.g. be applied to cell growth surfaces that are first dry. It is thereby possible to study the directed growth of neuronal axons or the chemotactic effects of cells.

The adhesive layer may have a thickness of 1 μm to 1000 μm, particularly 10 μm to 100 μm. This will establish a precise connection. The adhesive layer may particularly be made elastic.

In the above-described cover devices the sticky surface area may comprise a thermoplastic or a silicone, particularly PDMS. With these materials it is possible to produce such a cover device in an appropriate way. For instance, the surface area of a blank for the cover device may be coated with an adhesive comprising or consisting of one of the said materials. For instance, a coating with asymmetrically mixed PDMS may be provided.

The sticky surface area may be configured such that after connection to the sample carrier the cover device is again detachable from the sample carrier without any destruction and/or without any remains.

This makes it possible to connect a cover device to one or several sample carriers repeatedly.

The sticky surface area may be configured such that after connection to a coverslip the tensile strength is at least equal to the tensile strength of the reference material PDMS Sylgard 184, obtainable from Dow Corning, in a mixing ratio of 20:1 of base material to cross-linker. Such a minimum tensile strength, determined according to the protocol described hereinafter, is thus at least four times higher than the tensile strength of Sylgard 184 in a mixing ratio of 10:1. Particularly the tensile strength may be at least equal to twice and/or at the most equal to twenty times the tensile strength of the reference material.

To determine the tensile strength of the sticky surface of a cover device, a circular test cylinder is made from the material to be examined, with the circular base area of the cylinder used for the measurement having an rms roughness between 0.1 nm and 10 nm. For instance, when the tensile strength of a cover device made from a sticky material is determined, the test cylinder is made from said material. When the cover device comprises a blank provided with an adhesive layer, the test cylinder is made from the material of the blank with the above-mentioned roughness and the adhesive layer is applied (at the thickness used for the blank).

The round base area of the test cylinder has an area of 20 $mm^2$; the corresponding diameter is 5.4 mm. The cylinder is vertically suspended with the rotation-symmetrical axis such that the normal vector on the base area used for the test is oriented downwards. A conventional Menzel coverslip (with a width of 25.5 mm and a length of 75.5 mm) is glued to the base area from below, with the coverslip being provided with a weight. This information regards a test procedure at a gravitational acceleration of 9.81 $m/s^2$. To glue the coverslip to the base area, the coverslip is pressed onto the cylinder at a pressure of $3.0\times10^4$ Pa for 10 seconds.

The tensile strength follows from the total mass (including the mass of the coverslip) that remains stuck to the base area for at least 10 seconds before it detaches and falls off. It is determined at room temperature and at a relative humidity between 30% and 40%.

By comparison, a reference test cylinder is always made from the reference material Sylgard 184, Dow Corning, with the above-mentioned dimensions. In the reference test cylinder the mixing ratio of base material to cross-linker is 20:1. The reference test cylinder thereby comprises a sticky surface on which at least four times the mass, compared to a corresponding test cylinder of Sylgard 184 in a mixing ratio of 10:1, remains stuck for at least 10 seconds.

For each total mass (coverslip with weight) the method is carried out at least ten times. The retention time until detachment of the coverslip is here measured each time. A material to be tested has at least a tensile strength corresponding to a specific total mass if in the method for the specific total mass a mean retention time (with at least 10 runs) of at least 10 seconds has been obtained. This shall be applicable to both the reference material and the material to be tested.

The cover device and/or the sample carrier may comprise a plastic or glass. They can especially consist of this material. However, the cover devices and the sample carrier need not comprise the same material or the same type of material; this is just an option. The cover device may particularly consist of a sticky carrier material. Predetermined regions of the cover device may however have been treated such that the surface is no longer sticky in these regions. In principle, the whole cover device, part of the cover device, or only the sticky surface area may comprise or consist of a thermoplastic or a silicone. The cover device may be made of one piece.

The cover device may particularly be an injection molded part or comprise an injection molded blank. A surface area of the injection molded part or of the injection molded blank can then be treated such that a sticky surface area is provided.

The cover device may comprise an elastic material or consist of such a material. This may e.g. be an elastic thermoplastic. The elastic material may particularly show a Young's modulus of 1 kPa to 1 MPa, particularly from 1 kPa to 300 kPa. An elastic material makes it possible to adapt the cover device to the sample carrier in an appropriate way during the joining process.

In the previously described cover devices only part of the surface, particularly only part of the contact area with the sample carrier, may be made sticky. This can have the effect that surface areas that are e.g. needed for handling purposes are not sticky. Contact area with the sample carrier stands for the surface of the cover device that is designed or provided for connection to the sample carrier or rests on the sample carrier after connection. This partial stickiness can e.g. be achieved through the measure that only specific parts of a blank are provided with an adhesive layer or that a blank made of a sticky material is treated (e.g. passivated or plasma-treated) in areas that are in particular not part of the contact area with the sample carrier, in such a way that the surface is no longer sticky in these areas.

The invention particularly also provides a cover device for a sample carrier, comprising at least one cover element for covering a surface area of the sample carrier, the cover device being configured such that the surface area of the sample carrier is covered in a liquid-tight manner after connection of the cover device to the sample carrier. The at least one cover element thereby comprises a contact area with the sample carrier. Particularly the above-described cover devices may comprise at least one cover element of such a type.

At least a part of the sticky surface area of the cover device may be arranged on at least one cover element. This offers the possibility of connecting the cover element in a liquid tight manner to the sample carrier. In this case the sticky surface area is preferably arranged on the contact area of the cover element with the sample carrier. The sticky surface area can, but need not, be present or arranged on still other surface areas of the cover device.

The optional properties of at least one cover element, which are described here and in the following, may be applicable to one cover element, some cover elements or to every cover element.

As an alternative to the above-described variant, at least one cover element may be without a sticky surface area. To be more specific, the contact area of the cover element may then not be provided with a sticky surface. In this case the cover device comprises a sticky surface area in another area in such a way that the cover element achieves a liquid-tight covering.

At least one cover element may comprise an elastic material. It is thereby possible to accomplish a liquid-tight covering particularly by pressing the cover element onto the sample carrier during and after connection to the cover device. The elastic material may particularly have a Young's modulus between 1 kPa and 1 MPa, particularly 1 kPa to 300 kPa. This may be e.g. a thermoplastic or a silicone, particularly PDMS.

The elastic material may further be a sticky material. The sticky material may particularly be made non-curing and/or permanently sticky.

The cover device may comprise a substrate with a planar surface on which at least one cover element is arranged.

At least one cover element can particularly be configured such that the cover device is without a contact area in a region surrounding the at least one cover element (partly or completely), i.e. in this surrounding region and after connection to the sample carrier it does not rest thereon. To be more specific, the at least one cover element may have a cylindrical shape. The base area of the cylinder may in principle have any desired shape. For instance, the base area may be a circle or a polygon. Precisely defined surface areas can be covered by means of such cover elements in columnar form. A base area of the cylinder may here form a contact area.

As an alternative, or in addition, at least one cover element may be shaped in the form of a bar or web. When connected to a sample carrier, a cover element shaped in the form of a web thereby permits the formation of a boundary wall for a sample chamber or a reservoir. The web form may be designed to be straight or curved.

At least one cover element may have a height of 10 μm up to 30 mm, particularly 50 μm to 10 mm, preferably 100 μm to 3 mm. A cylindrical cover element may have a base area of 0.01 to 500 $mm^2$, particularly 0.1 to 50 $mm^2$. A cover element in web form may have a width of 50 μm to 30 mm, particularly 100 μm to 10 mm, and/or a length of more than 1 mm, particularly more than 10 mm.

At least one cover element may be configured such that it is compressed after connection of the cover device to the sample carrier. Due to the compressed state after the joining operation a liquid-tight cover can be achieved in an advantageous way.

In this case the at least one cover element may be configured such that its height after the joining process is reduced by 1% to 20%, particularly by 5% to 15%, as compared with the height before the joining process. This accomplishes an appropriate contact pressure for forming a liquid-tight covering.

The previously described cover devices may comprise a plurality of cover elements. The cover elements may have different or identical designs. For instance, the cover elements may have an identical shape with different dimensions. To be more specific, the cover device may comprise a plurality of cover elements in the form of cylinders having different base area dimensions. The height of the cover elements may be the same.

As a rule, the sample carrier to which the cover device is connected may be formed with or without structures, particularly with structured and/or unstructured surface areas. In the unstructured case it may have a planar surface or planar surface areas.

Particularly, the sample carrier may comprise a sample chamber or reservoir, and the cover device for covering a surface area may be formed in the interior of the sample chamber. To be more specific, the cover device may comprise at least one cover element for covering a surface area in the interior of the sample chamber. For this purpose the sample chamber may comprise an opening towards the surroundings. To be more specific, at least one cover element may be configured for covering a surface area on the bottom of the sample chamber.

The cover device may be configured such that it can be arranged completely in the interior of the sample chamber. The cover device is thus configured as an insert for a sample chamber. Furthermore, the cover device and/or at least one cover element may be configured such that a sample chamber and/or a cavity is formed by the cover device and/or by the at least one cover element after joining to the sample carrier. Said sample chamber (reservoir) and said cavity, respectively, may particularly be arranged in the interior of an (existing) sample chamber of the sample carrier. Furthermore, the cover device may be configured such that a channel is formed after connection to the sample carrier.

Part of the sticky surface area may be arranged such that after connection of the cover device to the sample carrier it is arranged outside the interior of the sample chamber. In particular, the whole sticky surface area can be arranged in such a way. This may prevent, for instance, adhesive residues from remaining in the interior of a sample chamber after the cover device has been removed.

For joining the cover device and the sample carrier the sticky surface can also be arranged alternatively or in addition on the sample carrier. Thus the invention also provides a sample carrier, comprising a sticky surface area for connection to a cover device, the sticky surface area being made sticky such that the sample carrier is covered in liquid-tight fashion after connection of the cover device to the sample carrier in the sticky surface area.

Such a sample carrier may, but not need, be used in combination with the previously described cover devices. The sample carrier can particularly comprise the above-described features as well.

Furthermore the invention provides a sample carrier system comprising a sample carrier and a cover device connected thereto, the cover device and/or the sample carrier being configured in the way as has been described above.

The sample carrier may comprise a foil or consist of such a foil. The foil may have a thickness of 1 μm to 250 μm, particularly 100 μm to 200 μm. The sample carrier may comprise a substrate with a planar surface having arranged thereon one or a plurality of sample chambers or reservoirs. As an alternative, one or a plurality of sample chambers may be arranged in the substrate. Particularly in order to form a sample chamber, the substrate may comprise a hole, for instance a blind hole or a through-hole. In the case of a blind hole the base of the blind hole forms the bottom of the sample chamber. Furthermore, the sample carrier may comprise a bottom plate which is connected to the substrate, for instance to form a bottom for a through-hole. The bottom plate may have a thickness of 1 μm to 1.5 mm; it can be configured in the form of a foil, as has particularly been described above.

The sample carrier may have one or a plurality of channels, formed e.g. in the substrate. The channels are preferably oriented at least in part in parallel with the base area of the sample carrier or the substrate. A substrate may have a planar surface in which at least one groove is formed. This surface is preferably opposite the surface on which one or several sample chambers are formed. A channel is formed by covering the at least one groove with a bottom plate.

The cover device, the sample carrier, the substrate and/or the bottom plate may be made of a plastic material or a silicone, particularly of predetermined autofluorescence, which is particularly less than or equal to the autofluorescence of COC or COP or of a conventional coverslip (for instance pure white glass of the hydrolytic class 1 (such as Menzel coverslip, particularly with thickness no. 1.5), and/or with a predetermined refractive index, particularly >1.2 and/or <1.7. With such a material of high optical quality microscopic analyses can be performed in an advantageous way. The substrate and/or the bottom plate, however, may also be made of glass. Furthermore, the cover device, the sample carrier, the substrate and/or the bottom plate are made flexible. All of the aforementioned elements may also be produced in an injection molding process.

Possible plastic materials are e.g. COC (cyclo-olefin-copolymer), COP (cyclo-olefin-polymer), PE (polyethylene), PS (polystyrene), PC (polycarbonate), or PMMA (polymethylmetacrylate). Sylgard 184, obtainable from Dow Corning, or other commercially available, cell-compatible, single- or multi-component silicones may be used as the silicone.

The cover device and/or the sample carrier may have the width and length of a conventional microscope slide (with a width of 25.5 mm and a length of 75.5 mm) or a multititer plate (85.5 mm×127.5 mm). The cover device and/or the sample carrier may have a height of 0.1 mm to 15 mm. In particular, the cover device may have a height of 1 mm to 3 mm. A substrate of a sample chamber may have a height of 0.1 mm to 5 mm, particularly of 1 mm to 2 mm, especially in a planar region.

A sample chamber or a channel of the sample carrier may have a void volume of 0.1 μl to 3 ml, particularly 20 μl to 2.5 ml. Sample chambers or channels formed in a substrate of a sample chamber can particularly have a void volume of 0.1 μl to 200 μl, particularly 20 μl to 150 μl. The height of such sample chambers or channels may be 5 μm to 1 mm, particularly 0.1 mm to 0.5 mm; the width may be 10 μm to 5 mm, particularly 0.5 mm to 2 mm. In sample chambers formed on a substrate, the height thereof may be 1 mm to 15 mm, particularly 5 mm to 10 mm.

Furthermore, the present invention provides a method for producing a cover device or a sample carrier, the method comprising the steps of:

- injection molding a blank made of a silicone or a thermoplastic;
- coating a predetermined surface area with an adhesive layer.

In this instance the blank can be made non-sticky. The adhesive may particularly be a pressure-sensitive adhesive. The adhesive may be a two-component adhesive having a base material and a cross-linker. Particularly base material and cross-linker can be mixed in an asymmetric ratio.

As an alternative, the present invention provides a method for making a cover device or a sample carrier, the method comprising the steps of:

- providing a blank made from a sticky material;
- treating a predetermined surface area to render the same no longer sticky.

Here, the blank may also be injection molded. The treatment of a sticky surface area to render the same no longer sticky may e.g. include passivation, particularly by means of plasma treatment.

The cover devices or sample carriers produced by means of this method may show the above-described properties and features.

BRIEF DESCRIPTION OF THE DRAWINGS

Further features and advantages shall now be described by way of the exemplary figures, in which.

DETAILED DESCRIPTION OF THE INVENTION

Figure 1:
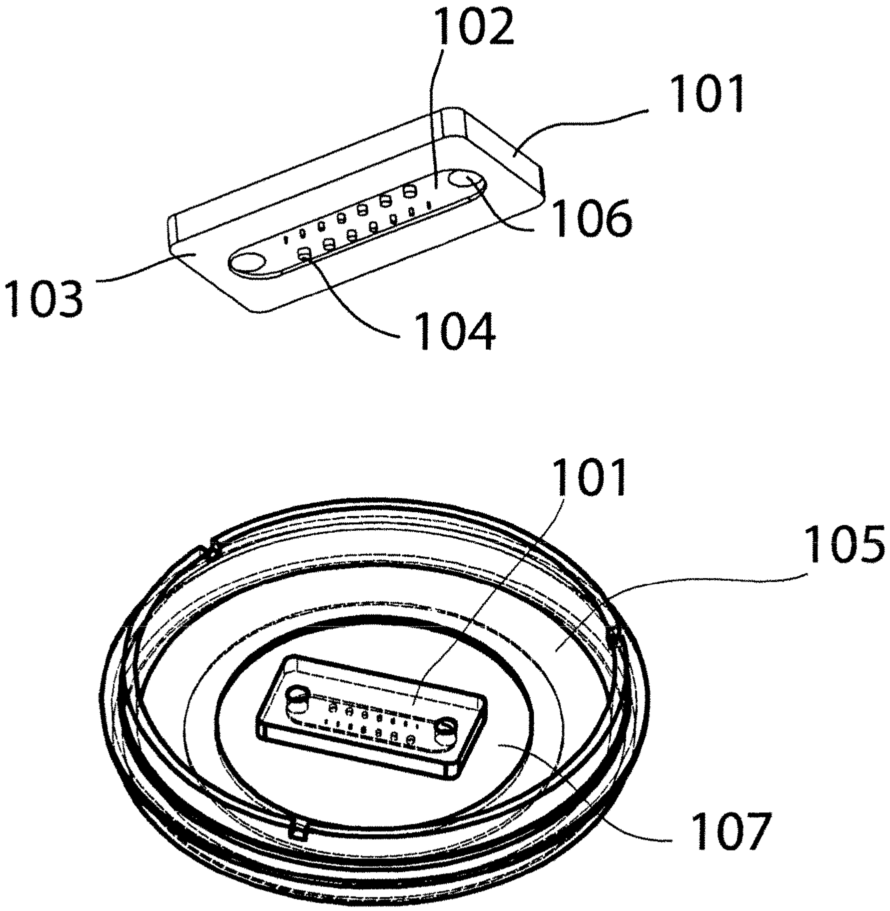
FIG. 1 shows an example of a cover device and of a sample carrier.

In the embodiment shown in FIG. 1, a cover device 101 is provided. The cover device 101 includes a recess 102 of predetermined height. This creates a surrounding rim by which a contact area 103 is formed.

The recess 102 has arranged therein a plurality of cover elements 104. These cover elements have the shape of circular cylinders of identical height. The cover elements, however, have different base area dimensions. For instance, the diameter of the base area may be 0.1 mm, 0.2 mm, 0.3 mm, 0.4 mm, 0.5 mm, 0.6 mm and 0.7 mm. There are two specimens of each circular cylinder, the cylindrical columns being arranged in two rows in opposite direction to even out possible fluidic impacts in the assays.

The cover device 101 is connected to a sample carrier 105 in liquid-tight fashion, as can be seen in the lower part of the figure. The sample carrier 105 is formed in the manner of a Petri dish, so that it comprises a sample chamber or reservoir. The cover device 101 is connected to the bottom 107 of the sample carrier and is thus entirely arranged inside the sample chamber.

After the connecting process both the rim 103 of the cover device and the cover elements 104 cover corresponding surface areas on the bottom 107 of the sample carrier 105 in a liquid-tight manner.

In the embodiment shown in FIG. 1, the recess 102 has further disposed therein two through-holes 106 with which after connection of the cover device to the sample carrier the resulting cavity can be filled and vented.

As a rule, the cover device should be configured such that it rests in a liquid-tight manner on a corresponding area of the sample carrier. The corresponding areas of the sample carrier may here be smooth, rough or porous. A smooth area has a roughness between 0.1 nm to 10 μm. A rough area has a roughness of more than 10 μm. A porous area may have pores with diameters of from 0.01 μm to 50 μm. Porous areas may particularly comprise filter membranes as are e.g. used for filtering microorganisms or for carrying out transmembrane migration assays.

For this purpose the cover device is preferably made from a silicone or a thermoplastic. For instance, the cover device may comprise an injection molded blank of silicone. The injection molded blank may e.g. be made from PDMS, e.g. Sylgard 184. In this two-component silicone a fully cross-linked state will be accomplished if the base material and the cross-linker are mixed in a ratio of 10:1; this is called symmetric with respect to the crosslinking-active groups in the base material and the cross-linker. In this instance the resulting material has a Young's modulus of 57 kPa. With such a mixing ratio the material is not sticky.

As a rule, the desired connection between cover device and sample carrier can be established when the whole contact area of the cover device or of the sample carrier is coated with a pressure-sensitive adhesive. As for the cover device, both the rim and the cylinder base areas of the cover elements 4 can be provided with the adhesive for this purpose.

Alternatively, however, the adhesive is only applied to the rim. The cover elements thus remain non-sticky. To achieve a liquid-tight covering, however, the cover elements are then made slightly higher than the depth of the recess 2 of the cover device.

For instance, the total thickness of the cover device may be 2 mm. The recess 2 may have a depth of 1 mm. The height of the columns 4 arranged in the recess 2 is however 1.1 mm, so that the columns project by 0.1 mm beyond the recess. The contact area of the rim is provided with an adhesive layer having a thickness of 10 μm.

When the cover device and the sample carrier are pressed against each other, this will create an adhesive bond. The cover elements are pressed against the sample carrier and get deformed, which results in a liquid-tight covering. During deformation the height of the cover elements is reduced in size. In the illustrated example the reduction is not more than 10%, which however depends on the question whether the areas of the cover device, on which the columns are arranged, get also deformed.

When the whole cover device is made from a homogeneous elastic material, the top (and the bottom, respectively) of the recess 102 will also get deformed. Alternatively, however, the cover device shows an inhomogeneous material distribution; in this instance the cover elements would exhibit a higher elasticity than the backside of the cover device.

A separate coating with an adhesive can be avoided if the material of the cover device or of the corresponding blank, respectively, is made sticky at least at specific places of the surface. For this purpose asymmetric mixtures of PDMS can e.g. be used. For a mechanically stable, but very sticky surface, mixing ratios of 20:1 to 60:1 (base material cross-linker) can be used. When Sylgard 184 is used, the adhesive can be removed from the sample carrier without remains after removal of the cover device at mixing ratios of 10:1 to 35:1.

As a rule, the cover device may also exhibit a variable mixing ratio, e.g. a mixing ratio gradient, over the thickness. The distribution of the mixing ratio can be chosen such that the side facing the sample carrier comprises sticky surfaces and is made more elastic. Stickiness and elasticity are decreasing in the direction of the side facing away from the sample carrier. Thus the side facing away from the sample carrier exhibits increased hardness to make the insert stable, which is also of help in the removal of the cover device.

According to an alternative manufacturing method the injection molded blank is made from an elastic thermoplastic with a Young's modulus of 1 kPa to 1 MPa. This blank can e.g. be made sticky by coating with sticky silicone or by means of plasma deposition. According to another possibility predetermined regions of the blank are coated with a sticky thermoplastic layer in a second injection molding step.

If a blank for the cover device is made from a substantially homogeneous sticky material, specific surface areas can be made non-sticky by passivation. A corresponding, spatially structured passivation can e.g. be accomplished through masked plasma treatment with the help of mask technology.

To be more specific, the embodiment shown in FIG. 1 makes it possible to cover circular areas with precisely predetermined diameters in a liquid-tight manner. As a rule, the cover elements, however, may also show other geometries. For instance, the base areas of the cylinder may have a polygonal shape. Furthermore, the cover elements may be shaped in the form of straight or curved webs, which have a width of a few μm to some mm. With such webs it is possible to form sample chambers or reservoirs separated from one another. The length of straight webs may be up to a few cm, depending on the requirements.

When such a cover device is connected to a sample carrier and when cells are subsequently seeded in or on the sample carrier, these cells will only get into contact with areas of the sample carrier that are not covered by the cover device. If the cells are of the type that can adhere to the bottom of a sample chamber, a confluent cell lawn can form that is bordered by the cover elements. When the cover devices are removed, the cells can also grow in the formerly covered areas of the sample carrier. With the analysis of such ingrowing processes, statements can be made on the behavior of the cells. This is particularly true when the ingrowth of the cells is analyzed as a function of the corresponding sample carrier surfaces (physical, chemical or biological properties, as are e.g. achieved by specific treatments), or as a function of substances in the cell suspension.

It is thus possible to carry out, for instance, so-called wound healing assays. Cover devices can here be used by which circles of different diameters (or other geometric figures) can be covered in one or several sample chambers. A corresponding cover device is shown in FIG. 1.

After the cover device has been removed from the sample carrier, in the sample chamber or chambers of which a confluent cell lawn is formed, quantitative statements can be made on cell growth (proliferation) owing to the different circle diameters. This offers the particular advantage that the cell growth need not be observed all the time (e.g. by means of video microscopy), but can be measured at a specific time on the basis of the diameter of the circle just overgrown.

Corresponding assays can particularly be carried out when multititer plates are used as sample carriers, the cover device then comprising cover elements for the corresponding sample chambers. A cover device can be made of one piece also for a multititer plate.

The described cover devices can further be used for the structured coating of surfaces. After the cover device has been connected to a sample carrier, identical or different coating substances can be filled into one or several sample chambers of the sample carrier to form corresponding surface functionalizations. Thus, after the cover device has been removed, one obtains sample chambers in which specific areas are surface-functionalized and others are not. When cell-adhesive coatings are used, a cell lawn can thus grow in specific areas only. The nutrient requirements of a cell culture can thus be reduced in a sample chamber, so that it can exist without any medium change over a long period of time, or can be kept in smaller vessels or in materials of less gas permeability.

So-called invasion assays offer a further field of application. A cover device is here applied to a homogeneously functionalized cell culture surface, e.g. plasma-treated polystyrene, the cover device being provided with webs as cover elements in such a way that after the joining operation one obtains two reservoirs separated by a separation wall. A monolayer of fibroblasts is thereafter grown in one of the reservoirs, and a monolayer of cancer cells in the other reservoir. After the cover device has been removed, two cell patches are present that are separated by a cell-free strip with a width predetermined by the thickness of the previously existing separation wall. Since the surface of the sample carrier is also functionalized in this region for cell adhesion, the cells can subsequently grow into the strip and interact with one another. Thus the invasion behavior or metastasis behavior of tumor cells in connective tissue can e.g. be studied, wherein e.g. specific cell staining is used in the form of fluorescence dyes to clearly distinguish the tumor cells from the fibroblasts.

The sample carrier can be made from one piece, e.g. in the form of a coverslip, a foil or a Petri dish. Alternatively, the sample carrier may comprise a substrate and a bottom plate connected thereto, with a groove being e.g. provided in the substrate, so that a channel is formed through the bottom plate. Alternatively or in addition, the substrate may comprise through-holes so that corresponding sample chambers or reservoirs are formed through the bottom plate.

The sample carrier may consist of a material similar or identical to the material of the cover device, or it may be wetted with a corresponding material. This allows an advantageous joining of the two elements.

The bottom plate may have a thickness of up to 2 mm. Thicknesses of up to 200 μm are particularly of advantage to the use of high-resolution microscopy. Larger thicknesses for low-resolution microscopy are used, as are e.g. employed in wound healing assays.

Bottom plates having a thickness in the range of 1 μm can be used in combination with the described cover devices, particularly for the laser microdissection of cell monolayers or of tissue pieces that can be fixed with the help of the sticky surfaces of the cover devices. Depending on the type, the areas that are not positioned on a tissue piece can also serve sealing and/or fixing purposes.

Figure 2:
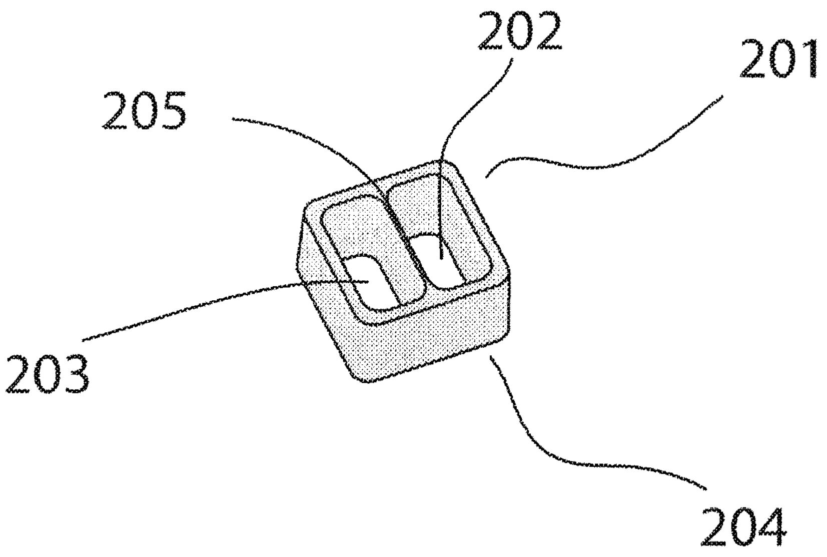
FIG. 2 shows a further example of a cover device.

A further example of a cover device 201 is shown in FIG. 2. The cover device is here intended as an insert for a sample chamber. The cover device 201 comprises a plurality of webs by which two sample chambers or reservoirs 202 and 203, which are separated by a separation wall 205, are formed after joining to a sample carrier. The lower area 204 of the cover device is made sticky, whereas the side walls and the upper area are not sticky to facilitate handling of the insert e.g. with tweezers or another gripping instrument.

Figure 3:
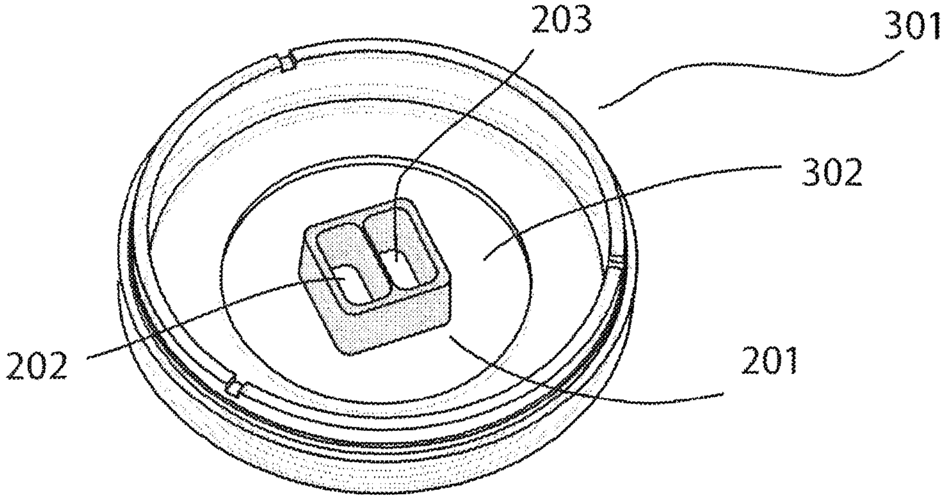
FIG. 3 shows a further example of a cover device and a sample carrier.

FIG. 3 shows a sample carrier system comprising the cover device 201 and a sample carrier 301. The cover device is connected in liquid-tight fashion via its sticky underside to the bottom 302 of the sample carrier. The two reservoirs 202 and 203 make it possible that cells are first grown separately and in the same volume after removal of the cover device. In the illustrated sample carrier the bottom 302 is preferably made from a material of high optical quality for high-resolution microscopy.

Figure 4:
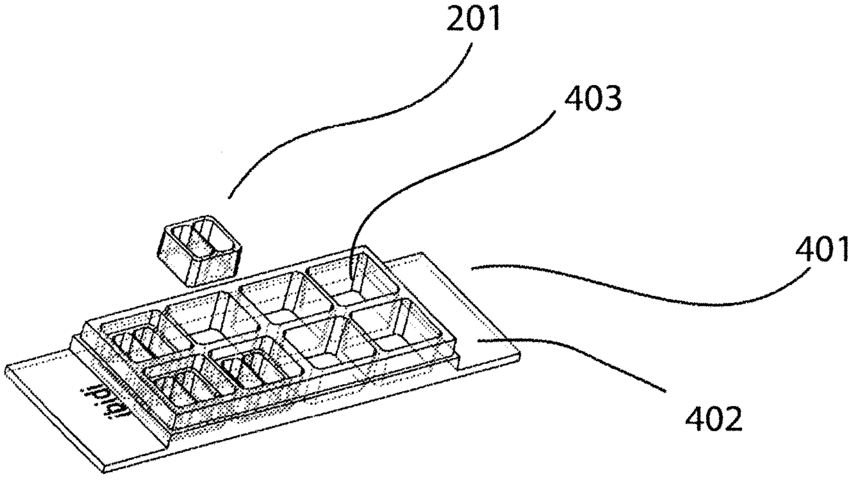
FIG. 4 shows a further example of a cover device and a sample carrier.

FIG. 4 illustrates a further example of a sample carrier system with a sample carrier 401; in this instance, with several cover devices 201. The sample carrier comprises a substrate 402 with a planar surface on which a plurality of sample chambers (reservoirs) 403 are arranged. An insert 201 can be introduced into the interior of each sample chamber 403 so as to produce two (partial) reservoirs in this way each time. Each insert is connected on its underside to the bottom of the respective sample chamber 403 in a liquid-tight manner. In the resulting partial sample chambers corresponding assays can then be carried out, as has been described above.

Figure 5:
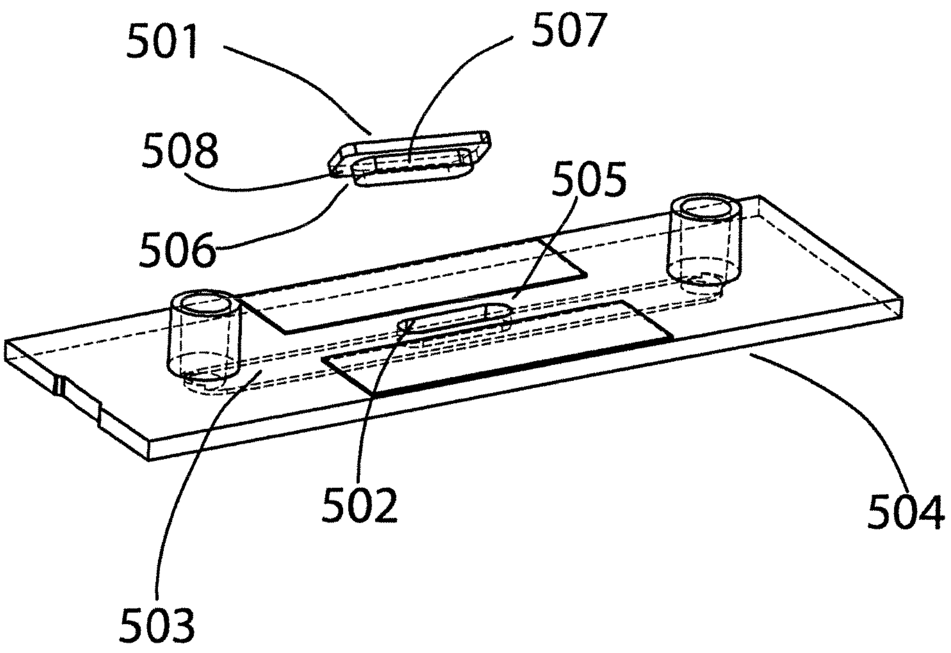
FIG. 5 shows a further example of a cover device and of a sample carrier.

FIG. 5 shows a further example of a cover device 501. The cover device 501 comprises a substrate with a planar surface 508 on which a cover element 506 is arranged. A sample carrier 504 comprises a substrate with a planar surface on which two sample chambers are arranged that are interconnected via a channel 503 disposed in the substrate. Due to the channel a sample chamber is again formed in the substrate. The channel 503 can for instance be formed by a groove which is introduced into the underside of the substrate and covered with a foil.

The substrate of the sample carrier has formed therein an opening 502 leading into channel 503. The side wall of the opening 502 can be made perpendicular or conical. Depending on the requirements, the cover element 506 is formed such that it fills the opening partly or completely. Particularly the sides 507 of the cover element 506 rest in part or completely on the side wall. The planar surface 508 of the substrate of the cover device is made sticky to connect the cover device in this area in a liquid-tight manner to the sample carrier. The opening 502 can thereby be closed.

According to an alternative the substrate of the cover device of FIG. 5 can also be omitted. In this instance, the sides 507 would for example be made sticky to connect the cover device in a liquid-tight manner to the sample carrier.

It goes without saying that the above-described embodiments shall only be understood as examples and that the individual features can also be combined with one another in a different way.

The invention claimed is:

1. A sample carrier system comprising:

a sample carrier, wherein the sample carrier includes a sample chamber formed of a bottom plate and a side wall;

a cover device, wherein the cover device comprises:

a sticky surface area for connection to a first surface area of the sample carrier, wherein the sticky surface area is configured such that (i) a covered portion of the sample carrier is covered in liquid-tight fashion by connection of the sticky surface area of the cover device to the first surface area of the sample carrier, and (ii) the sticky surface area is permanently sticky to permit repeated joining of the cover device to the sample carrier; and at least one cover element for covering a second surface area of the sample carrier, wherein the at least one cover element is configured such that the second surface area of the sample carrier is covered in liquid-tight fashion by connection of the cover device to the sample carrier, by connecting the at least one cover element to the second surface area;

wherein the cover device is not in contact with the side wall of the sample chamber when the cover device is arranged in the sample chamber;

wherein covering the second surface area includes contacting the second surface area;

wherein the second surface area is arranged in the interior and on the bottom plate of the sample chamber;

wherein the sticky surface area is configured such that after connection to the sample carrier, the cover device is again detachable therefrom without any destruction and/or without any remains; and wherein (i) at least a part of the sticky surface area of the cover device is arranged on the at least one cover element such that the first surface area includes the second surface area, or (ii) the at least one cover element is without a sticky surface, such that the first surface area is separate from the second surface area.

2. The sample carrier system according to claim 1, wherein the cover device comprises a carrier material to which an adhesive layer having a thickness of 1 μm to 1000 μm is applied for forming the sticky surface area.

3. The sample carrier system according to claim 1, wherein the sticky surface area comprises a thermoplastic or a silicone.

4. The sample carrier system according to claim 1, wherein at least one selected from a group comprising the cover device and the sample carrier comprise a plastic or glass.

5. The sample carrier system according to claim 1, wherein the cover device consists of a sticky carrier material.

6. The sample carrier system according to claim 1, wherein at least part of the sticky surface area is arranged on at least one of the cover elements.

7. The sample carrier system according to claim 1, wherein at least one of the cover elements is without a sticky surface area.

8. The sample carrier system according to claim 1, wherein at least one of the cover elements comprises an elastic material.

9. The sample carrier system according to claim 1, wherein part of the sticky surface area is arranged such that after connection of the cover device to the sample carrier it is arranged outside an interior of the sample chamber.

10. The sample carrier system according to claim 1, wherein the sticky surface areas comprises PDMS.

11. A sample carrier system comprising:

a sample carrier, wherein the sample carrier includes a sample chamber formed of a bottom plate and a side wall;

a cover device, wherein the cover device comprises:

a sticky surface area for connection to a first surface area of the sample carrier, wherein the sticky surface area is configured such that (i) a covered portion of the sample carrier is covered in liquid-tight fashion by connection of the sticky surface area of the cover device to the first surface area of the sample carrier, and (ii) the sticky surface area is permanently sticky to permit repeated joining of the cover device to the sample carrier; and at least one cover element for covering a second surface area of the sample carrier, wherein the at least one cover element is configured such that the second surface area of the sample carrier is covered in liquid-tight fashion by connection of the cover device to the sample carrier, by connecting the at least one cover element to the second surface area;

wherein the cover device further comprises a plurality of webs by which at least two self-contained reservoirs are formed after joining the cover device to the sample chamber, each reservoir separated from one another by a separation wall;

wherein covering the second surface area includes contacting the second surface area;

wherein the second surface area is arranged in the interior and on the bottom plate of the sample chamber;

wherein the sticky surface area is configured such that after connection to the sample carrier, the cover device is again detachable therefrom without any destruction and/or without any remains; and wherein at least a part of the sticky surface area of the cover device is arranged on the at least one cover element such that the first surface area includes the second surface area, or the at least one cover element is without a sticky surface, such that the first surface area is separate from the second surface area.

12. The sample carrier system according to claim 11, wherein the cover device comprises a carrier material to which an adhesive layer having a thickness of 1 μm to 1000 μm is applied for forming the sticky surface area.

13. The sample carrier system according to claim 11, wherein the sticky surface area comprises a thermoplastic or a silicone.

14. The sample carrier system according to claim 11, wherein at least one selected from a group comprising the cover device and the sample carrier comprise a plastic or glass.

15. The sample carrier system according to claim 11, wherein the cover device consists of a sticky carrier material.

16. The sample carrier system according to claim 11, wherein at least part of the sticky surface area is arranged on at least one of the cover elements.

17. The sample carrier system according to claim 11, wherein at least one of the cover elements is without a sticky surface area.

18. The sample carrier system according to claim 11, wherein at least one of the cover elements comprises an elastic material.

19. The sample carrier system according to claim 11, wherein at least one of the cover elements has a cylindrical form or a bar shape including a separation wall.

20. The sample carrier system according to claim 11, wherein at least one of the cover elements is configured such that it is compressed after connection of the cover device to the sample carrier.

* * * * *